May 13, 1952 W. T. KIRKMAN Plant Pat. 1,096
NECTARINE TREE
Filed Oct. 12, 1950
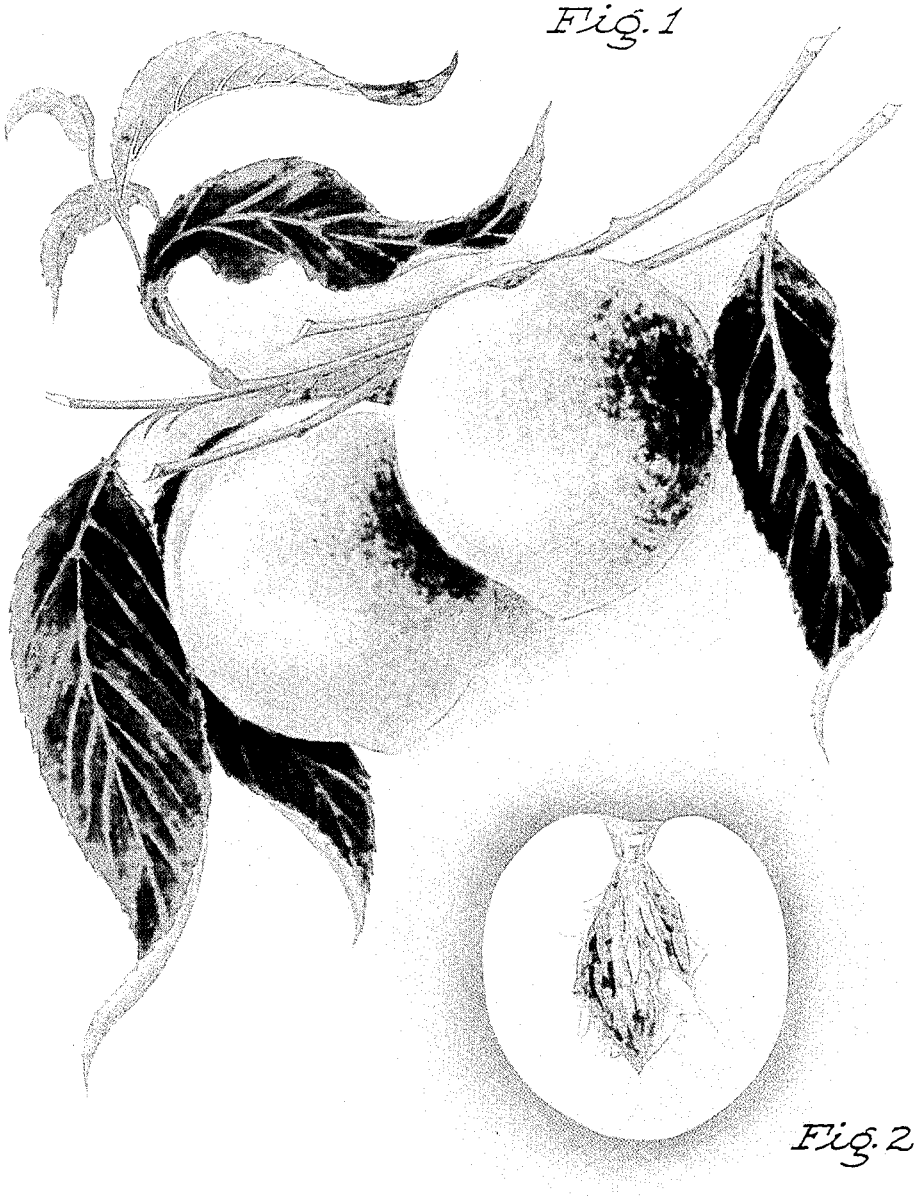
WITNESS
Addison J. Avery
INVENTOR
William T. Kirkman
Herbert Herbert
ATTYS Patented May 13, 1952

Plant Pat. 1,096

UNITED STATES PATENT OFFICE 1,096

NECTARINE TREE

William T. Kirkman, Madera, Calif., assignor to
John M. Garabedian, Fresno, Calif.

Application October 12, 1950, Serial No. 189,723

1 Claim. (Cl. 47—62)

This discovery relates to a new and distinct variety of nectarine whose fruit is especially adapted for market or commercial use.

The variety is an open pollinated seedling of the Quetta nectarine but distinguishes therefrom by a ripening period four to five weeks later than the Quetta; is much firmer of flesh; does not soften at the tip as does the Quetta; and is rounder and smoother.

A substantial number of Quetta nectarine seeds were planted in my orchard near Madera, California, followed by a second generation planting; the trees of the second generation planting, as well as those of the first generation, while open-pollenated, having been made the subject of careful and continued inspection by me, together with selection wth respect to desirable pomological characteristics.

The instant variety is one of said second generation trees, having been recognized by me as being new and distinct, and as having desirable characteristics for commercial reproduction.

Since its discovery the new variety has been successfully asexually reproduced by budding onto suitable root stock growing in my experimental orchard aforesaid; the reproductions carrying forward all of the distinctive characteristics of the parent tree and its fruit.

In the drawings:

Fig. 1 is a perspective view of two of the nectarines of the new variety in connection with twigs and leaves.

Fig. 2 is a sectional view taken axially of one of the fruit, with the stone exposed.

Referring now in detail to the new and distinct variety of nectarine tree and its fruit, the following is a specific description, in outline, of the same; detailed identification of colors being by reference to Maerz and Paul Dictionary of Color:

Tree: Large; vigorous; upright and spreading; dense; round topped; hardy; medium productive; regular bearer.

Trunk: Stocky; smooth.

Branches: Stocky; smooth. Color—brown. *Lenticels*—medium to few; medium size.

Leaves: Size—medium. Average length—5⅝″; average width—1½″; lanceolate; medium thick; smooth. Color—dark green (22-L-9) on top, with lighter green (21-J-5) on the under side. *Leaf twigs.*—Color—light yellowish green (19-K-4).

*Margin.*—Glandular—crenate.

*Petiole.*—Medium length; medium thickness.

*Glands.*—On base of blade or petiole just below the blade. Average—two in number; opposite; small; reniform. Color—green. No stipules.

Flower buds: Half hardy. Size—medium to small; length—medium to short. Obtuse; plump; free; pubescent.

Flowers: First and full bloom on or about March 1st and 12th, respectively. Medium blooming period. Size—small; color—dark pink.

Fruit: Maturity when described—hard, August 10, 1950. Dates of first and last picking—August 7, 1950, and August 24, 1950, respectively. Size—large to medium. Uniform—average 2⅜″ axially and 2⅜″ transversely in the suture plane. Form—uniform; symmetrical; broadly ovoid.

*Suture.*—Shallow; extends from base to apex.

*Ventral surface.*—Rounded to abrupt; elongated in suture plane; average depth—½″; average breadth—⅞″.

*Base.*—Rounded.

*Apex.*—Rounded.

*Pistil point.*—Apical (a very short small tip).

Skin: Medium thickness; tough; somewhat astringent; tenacious to flesh; tendency to crack—none. Color—a yellowish ground color (9-K-1), blushed red on the sunny side (3-K-2, shading into 5-L-6). Down—wanting.

Flesh:

*Color.*—White to creamy white (9-D-1, shading into 9-C-2).

*Amygdalin.*—Abundant.

*Texture.*—Firm, meaty.

*Fibers.*—Few, fine, tender.

*Ripens.*—Evenly.

*Flavor.*—Sub-acid—somewhat vinous.

*Aroma.*—Distinct.

*Eating quality.*—Good.

Stone: Cling. Adheres to flesh over entire surface.

*Size.*—Medium. Average length 1½″; average thickness ¾″.

*Form.*—Obovoid—full toward apex.

*Base.*—Straight.

*Hilum.*—Oval.

*Apex.*—Rounded—acuminate tip.

*Sides.*—Equal.

*Surface.*—Irregularly furrowed throughout.

*Ridges.*—Rounded.

*Dorsal edge.*—Narrow, with shallow groove throughout.

*Ridges.*—Continuous.

*Color.*—Purplish red (46–L–1).
*Tendency to split.*—Slight.

The described new variety of nectarine tree bears fruit characterized by good keeping and shipping qualities.

The fruit of the new variety is well adapted for commercial or market use, having an attractive appearance, and being quite tasty. As compared to the Quetta nectarine, which it most closely resembles, the present variety bears fruit which ripens four to five weeks later; does not soften at the tip as does the Quetta; is rounded rather than elongated as the Quetta; and is much smoother in skin texture.

The tree and its fruit herein described may vary in slight detail due to climatic and soil conditions under which the variety may be grown.

Having thus described the discovery, I claim:

A new and distinct variety of nectarine tree substantially as described and illustrated, bearing white to creamy white fleshed clingstone fruit, characterized by a ripening period approximately four to five weeks later than the Quetta variety, and distinguished from the latter by firmer flesh; rounder shape; and smoother skin.

WILLIAM T. KIRKMAN.

No references cited.